US00PP15273P2

(12) United States Plant Patent
Larsen

(10) Patent No.: US PP15,273 P2
(45) Date of Patent: Oct. 26, 2004

(54) ***OSTEOSPERMUM* PLANT NAMED 'SUNNY CECIL'**

(50) Latin Name: *Osteospermum ecklonis*
Varietal Denomination: Sunny Cecil

(76) Inventor: Bjarne Nyholm Larsen, Grönnegyden 148, DK-5270 Odense N (DK)

( * ) Notice: Subject to any disclaimer, the term of this patent is extended or adjusted under 35 U.S.C. 154(b) by 0 days.

(21) Appl. No.: 10/743,063

(22) Filed: Dec. 22, 2003

(51) Int. Cl.[7] ..... A01H 5/00
(52) U.S. Cl. ..... Plt./360
(58) Field of Search ..... Plt./360

(56) References Cited

PUBLICATIONS

UPOV–ROM GTITM, Plant Variety Database, 2004/01, GTI jouve Retrieval Software, Citation for *Osteospermum* 'Sunny Cecil'.*

* cited by examiner

*Primary Examiner*—Anne Marie Grunberg
*Assistant Examiner*—June Hwu
(74) *Attorney, Agent, or Firm*—C. A. Whealy

(57) ABSTRACT

A new and distinct cultivar of *Osteospermum* plant named 'Sunny Cecil', characterized by its compact, upright and mounded plant habit; dense and bushy growth habit; freely flowering habit; and white-colored ray florets and dark purple-tipped disc florets.

2 Drawing Sheets

Botanical classification/cultivar designation: *Osteospermum ecklonis* cultivar Sunny Cecil.

BACKGROUND OF THE INVENTION

The present Invention relates to a new and distinct cultivar of *Osteospermum* plant, botanically known as *Osteospermum ecklonis,* and hereinafter referred to by the name 'Sunny Cecil'.

The new *Petunia* is a product of a planned breeding program conducted by the Inventor in Odense, Denmark. The objective of the breeding program is to create new compact *Osteospermums* with continuous flowering, good postproduction longevity and attractive flower coloration.

The new *Osteospermum* originated from a self-pollination made by the Inventor in 2001 of the *Osteospermum ecklonis* cultivar Sunny Gustaf, disclosed in U.S. Plant Pat. No. 10,670.

The new *Osteospermum* was discovered and selected by the Inventor as a single flowering plant within the resulting progeny from the self-pollination in a controlled environment in Odense, Denmark.

Asexual reproduction of the new *Osteospermum* by terminal vegetative cuttings was first conducted in Odense, Denmark. Asexual reproduction by cuttings has shown that the unique features of this new *Osteospermum* are stable and reproduced true to type in successive generations.

SUMMARY OF THE INVENTION

The cultivar Sunny Cecil has not been observed under all possible environmental conditions. The phenotype may vary somewhat with variations in environment such as temperature, daylength and light intensity without, however, any variance in genotype.

The following traits have been repeatedly observed and are determined to be the unique characteristics of 'Sunny Cecil'. These characteristics in combination distinguish 'Sunny Cecil' as a new and distinct *Osteospermum*:

1. Compact, upright and mounded plant habit.
2. Dense and bushy growth habit.
3. Freely flowering habit.
4. White-colored ray florets and dark purple-tipped disc florets.

Compared to plants of the parent, the cultivar Sunny Gustaf, plants of the new *Osteospermum* are more compact, have lighter green-colored leaves, are more freely flowering, have larger inflorescences, and have shorter and stronger peduncles.

Plants of the new *Osteospermum* can be compared to plants of the cultivar Sunny Martha, disclosed in U.S. Plant Pat. No. 10,978. In side-by-side comparisons conducted in Fyn, Denmark, plants of the new *Osteospermum* differed from plants of the cultivar Sunny Martha in the following characteristics:

1. Plants of the new *Osteospermum* were more upright and not as outwardly spreading as plants of the cultivar Sunny Martha.
2. Plants of the new *Osteospermum* and the cultivar Sunny Martha differed in ray floret coloration as plants of the cultivar Sunny Martha had light lavender-colored ray florets.
3. Plants of the new *Osteospermum* had longer and sturdier peduncles than plants of the cultivar Sunny Martha.

BRIEF DESCRIPTION OF THE PHOTOGRAPHS

The accompanying colored photographs illustrate the overall appearance of the new *Osteospermum* showing the colors as true as it is reasonably possible to obtain in colored reproductions of this type. Colors in the photographs may differ from the color values cited in the detailed botanical description which accurately describe the colors of the new *Osteospermum*.

The photograph on the first sheet comprises a side perspective view of a typical flowering plant of 'Sunny Cecil' grown in a 11-cm container.

The photograph on the second sheet is a close-up view of the under surface of a typical inflorescence, the upper surface of a typical inflorescence, the upper surface of a typical fully expanded leaf, and the upper surface of a typical developing leaf of 'Sunny Cecil'.

DETAILED BOTANICAL DESCRIPTION

The aforementioned photographs and following observations and measurements describe plants grown in Fyn, Denmark, in a glass-covered greenhouse during the spring and early summer. After planting rooted cuttings, plants were grown for about 20 weeks in 11-cm containers. During the first five weeks of production of the plants, day and night temperatures were about 20° C., then temperatures were reduced to 14° C. Color references are made to The Royal Horticultural Society Colour Chart, $4^{th}$ Edition, except where general terms of ordinary dictionary significance are used.

Botanical classification: *Osteospermum ecklonis* cultivar Sunny Cecil.

Parentage: Self-pollination of *Osteospermum ecklonis* cultivar Sunny Gustaf, disclosed in U.S. Plant Pat. No. 10,670.

Propagation:

*Type.*—Terminal vegetative cuttings.

*Time to initiate rooting.*—About 10 to 14 days at 18 to 21° C.

*Root description.*—Fine, fibrous and branching.

Plant description:

*Appearance.*—Perennial herbaceous container and garden plant. Compact, upright and mounded plant habit. Freely branching; dense and bushy growth habit. Moderately vigorous to vigorous growth rate.

*Plant height.*—About 20 cm.

*Plant width or area of spread.*—About 17 to 20 cm.

*Lateral branches.*—Quantity per plant: About four primary lateral branches and about 17 secondary lateral branches. Length, primary branches: About 3 cm. Length, secondary branches: About 17 to 20 cm. Diameter, primary and secondary branches: About 4 to 5 mm. Internode length: About 3 mm. Aspect: Mostly upright to about 10° from vertical. Strength: Strong, sturdy. Texture: Smooth, glabrous. Color: 144C.

*Foliage description.*—Arrangement: Alternate; simple. Length: About 3 to 7 cm. Width: About 1 to 4 cm. Shape: Obovate to lanceolate. Apex: Obtuse. Base: Attenuate. Margin: Broadly serrate. Venation pattern: Pinnate. Texture, upper and lower surfaces: Pubescent; scattered short, stiff hairs. Color: Developing foliage, upper surface: 147A. Developing foliage, lower surface: 148C. Fully expanded foliage, upper surface: 139B; venation, same as lamina. Fully expanded foliage, lower surface: 147A; venation, 148B. Petiole: Length: About 1 to 3 cm. Diameter: About 2 to 4 mm. Texture, upper and lower surfaces: Smooth. Color, upper and lower surfaces: 145B.

Inflorescence description:

*Appearance.*—Terminal and axillary inflorescences held above and beyond the foliage on moderately strong and sturdy peduncles. Composite inflorescence form, radially symmetrical, with lanceolate-shaped ray florets and disc florets massed at the center; ray and disc florets develop acropetally on a capitulum. Inflorescences persistent. Inflorescences face mostly upright to about 10° from vertical.

*Flowering response.*—Plants flower continuous and freely from the spring through the fall.

*Postproduction longevity.*—Inflorescences maintain good color and substance for about five to nine days on the plant.

*Quantity of inflorescences per plant.*—Freely flowering; about 25 to 30 buds and open inflorescences.

*Fragrance.*—Faint; fresh, lemon-like.

*Inflorescence diameter.*—About 6 to 7 cm.

*Disc diameter.*—About 1.5 cm.

*Inflorescence buds.*—Length: About 1.2 cm. Diameter: About 1 cm. Shape: Globular. Color: Towards the base, 145C; towards the apex, 146B.

*Ray florets.*—Length: About 2.5 to 2.8 cm. Width: About 8 mm. Shape: Lanceolate. Apex: Acute. Base: Acute. Margin: Entire. Texture, upper and lower surfaces: Smooth, satiny. Orientation: Initially upright then about 60° from vertical. Number of ray florets per inflorescence: About 18 in one whorl. Color: When opening and fully opened, upper surface: Close to 155D. When opening and fully opened, lower surface: Ground color, 155D, with fine longitudinal stripes, 140D to 141A.

*Disc florets.*—Shape: Tubular, elongated. Apex: Five-pointed. Length: About 8 mm. Width: At apex, about 2 mm; at base, about 1 mm. Number of disc florets per inflorescence: About 50. Color, immature: N186A. Color, mature: N155D tipped with N187A.

*Phyllaries.*—Quantity per inflorescence: About 15. Length: About 6 to 12 mm. Width: About 1 to 3 mm. Shape: Lanceolate. Apex: Acuminate. Base: Fused. Margin: Entire. Color: 137D.

*Peduncles.*—Length: About 7 to 10 cm. Diameter: About 2 mm. Strength: Moderately strong; sturdy. Texture: Smooth. Color: 144C.

*Reproductive organs.*—Androecium: Stamen number: Five per floret; fused around style. Anther shape: Linear. Anther length: About 2 mm. Anther color: N99B. Pollen amount: Abundant. Pollen color: N25B. Gynoecium: Pistil number: One per floret. Pistil length: About 4 mm. Pistil color: N187A. Style length: About 2 mm. Stigma shape: Two-parted. Stigma color: N187A. Ovary color: 2D.

*Seed.*—Length: About 2 to 3 mm. Diameter: About 1 mm.

Disease/pest resistance: Resistance to pathogens and pests common to *Osteospermums* has not been observed on plants grown under commercial greenhouse or outdoor conditions.

Weather tolerance: Plants of the new *Osteospermum* have been observed to tolerate drought, rain, wind, and temperatures from about 1 to 35° C.

What is claimed is:

1. A new and distinct cultivar of *Osteospermum* plant named 'Sunny Cecil', as illustrated and described.

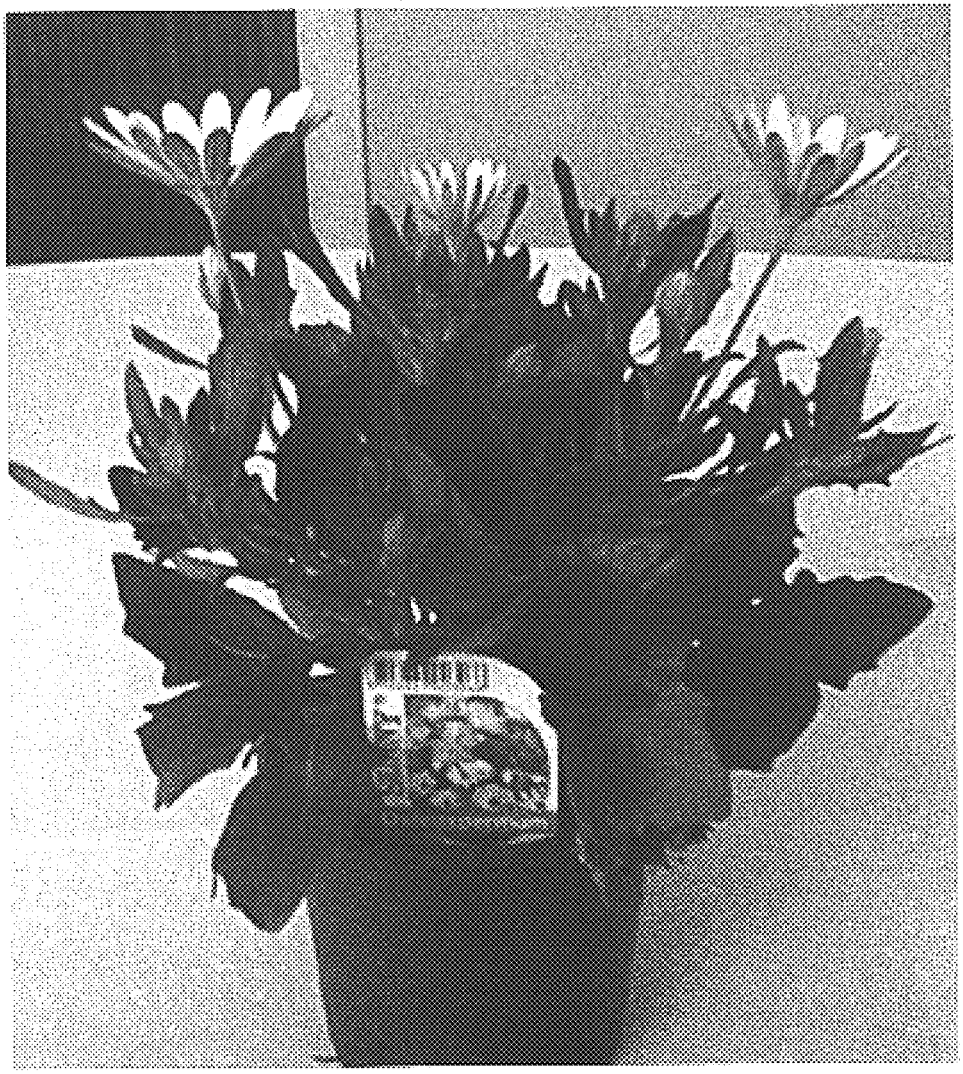

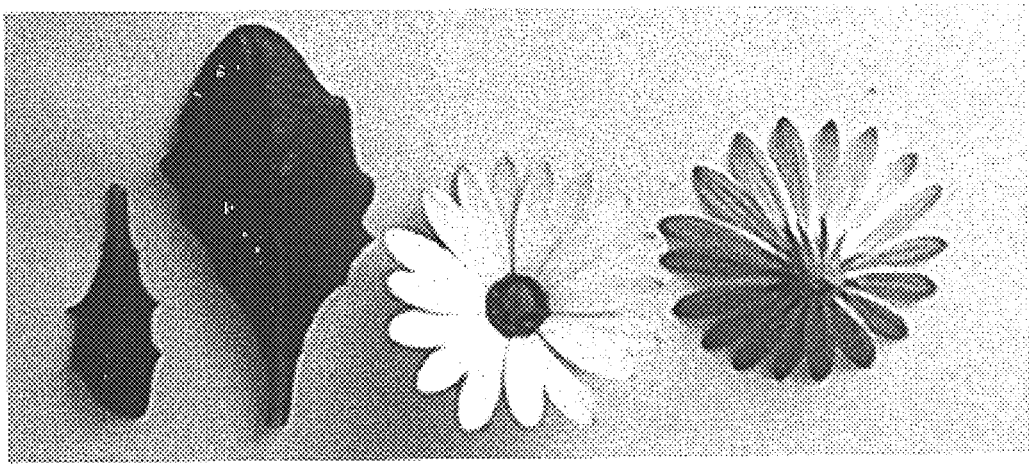

* * * * *